United States Patent

Porter et al.

(10) Patent No.: US 6,534,513 B1
(45) Date of Patent: Mar. 18, 2003

(54) PHENYLALKANOIC ACID DERIVATIVES

(75) Inventors: John Robert Porter, Chinnor (GB); Graham John Warrellow, Northwood (GB); Sarah Catherine Archibald, Maidenhead (GB); John Clifford Head, Maidenhead (GB)

(73) Assignee: Celltech R&D Limited, Slough (GB)

( * ) Notice: Subject to any disclaimer, the term of this patent is extended or adjusted under 35 U.S.C. 154(b) by 0 days.

(21) Appl. No.: 09/408,243

(22) Filed: Sep. 29, 1999

(51) Int. Cl.$^7$ .................. A61K 41/435; A61K 31/44; C07D 213/46; C07D 213/81; C07C 229/00
(52) U.S. Cl. .................. 514/277; 514/354; 546/314; 546/323; 562/490; 562/455
(58) Field of Search ................ 562/440, 455; 546/314, 323; 514/277, 354

(56) References Cited

U.S. PATENT DOCUMENTS

| | | | |
|---|---|---|---|
| 4,470,973 A | 9/1984 | Natarajan et al. | 424/177 |
| 4,554,273 A | 11/1985 | Bayssat et al. | 514/221 |
| 4,987,132 A | 1/1991 | Mase et al. | 514/252 |
| 5,164,372 A | 11/1992 | Matsuo et al. | 514/19 |
| 5,227,490 A | 7/1993 | Hartman et al. | |
| 5,260,277 A | 11/1993 | McKenzie | 544/18 |
| 5,296,486 A | 3/1994 | Lazer et al. | 514/333 |
| 5,399,585 A | 3/1995 | Alig et al. | 514/438 |
| 5,510,346 A | 4/1996 | Martin et al. | 514/221 |
| 5,698,691 A | 12/1997 | Yukimasa et al. | 540/490 |
| 5,773,646 A | 6/1998 | Michael et al. | |
| 5,952,381 A * | 9/1999 | Chen et al. | |
| 6,093,696 A | 7/2000 | Head et al. | 514/19 |

FOREIGN PATENT DOCUMENTS

| | | |
|---|---|---|
| DE | 23 16 881 A | 10/1973 |
| DE | 28 37 264 A1 | 3/1979 |
| DE | 196 54 483 A | 1/1998 |
| EP | 0 031 104 A1 | 7/1981 |
| EP | 0 048 763 A1 | 4/1982 |
| EP | 0 144 230 A | 6/1985 |
| EP | 0 288 176 A | 10/1988 |
| EP | 0 322 068 A1 | 6/1989 |
| EP | 0 394 989 A2 | 10/1990 |
| EP | 0 498 268 A2 | 8/1992 |
| EP | 0 596 406 A1 | 5/1994 |
| EP | 0 710 657 A1 | 5/1996 |
| EP | 0 710 659 A1 | 5/1996 |
| EP | 0 842 943 A2 | 5/1998 |
| EP | 0 842 945 A2 | 5/1998 |
| JP | 56 090045 | 7/1981 |
| JP | 03 135962 | 6/1991 |
| WO | WO 86/02353 | 4/1986 |
| WO | WO 93/00095 | 1/1993 |
| WO | WO 93/08174 | 4/1993 |
| WO | WO 93/09795 | 5/1993 |
| WO | WO 94/15954 | 7/1994 |
| WO | WO 94/15955 | 7/1994 |
| WO | WO 94/29285 | 12/1994 |
| WO | WO 95/13811 | 5/1995 |
| WO | WO 95/15973 | 6/1995 |
| WO | WO 95/19356 | 7/1995 |
| WO | WO 95/35314 | 12/1995 |
| WO | WO 96/01644 | 1/1996 |
| WO | WO 96/22966 | 8/1996 |
| WO | WO 96/26190 | 8/1996 |
| WO | WO 97/03094 | 1/1997 |
| WO | WO 97/04247 | 2/1997 |
| WO | WO 97/08145 | 3/1997 |
| WO | WO 97/12866 | 4/1997 |

(List continued on next page.)

OTHER PUBLICATIONS

Yanagisawa, H. et al., WO 97/37970, "Preparation of phenylalkylcarboxylic acid derivatives lowering blood sugar level," *Chemical Abstracts*, 1997, Abstract 127:307307, 4 pages.

Clausen, K., et al., "Studies on amino acids and peptides. II. Synthesis of protected endothiodepeptides," *J. Chem. Scr.*, 1982, 20(1–2), 14–18, doc. No. 97:163474 (abstract only, 1 page).

(List continued on next page.)

*Primary Examiner*—Johann Richter
*Assistant Examiner*—Paul A. Zucker
(74) *Attorney, Agent, or Firm*—Woodcock Washburn LLP

(57) ABSTRACT

Phenylalkanoic acid derivatives of formula (1) are described:

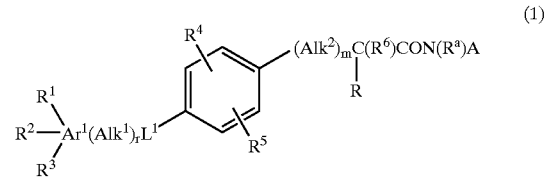

wherein

Ar$^1$ is an aromatic or heteroaromatic group;

L$^1$ is a covalent bond or a linker atom or group;

A is an optionally substituted aliphatic, heteroaliphatic, cycloaliphatic, polycycloaliphatic, heterocycloaliphatic, polyheterocycloaliphatic, aromatic or heteroaromatic group;

R is a carboxylic acid (—CO$_2$H) or a derivative thereof;

and the salts, solvates, hydrates and N-oxides thereof. The compounds are able to inhibit the binding of alpha 4 integrins to their ligands and are of use in the prophylaxis and treatment of immune or inflammatory disorders.

9 Claims, No Drawings

FOREIGN PATENT DOCUMENTS

| | | |
|---|---|---|
| WO | WO 97/23480 | 7/1997 |
| WO | WO 97/24124 | 7/1997 |
| WO | WO 97/31907 | 9/1997 |
| WO | WO 97/36858 | 10/1997 |
| WO | WO 97/36859 | 10/1997 |
| WO | WO 97/36861 | 10/1997 |
| WO | WO 97/36862 | 10/1997 |
| WO | WO 97/44333 | 11/1997 |
| WO | WO 97/47618 | 12/1997 |
| WO | WO 98/00395 | 1/1998 |
| WO | WO 98/04247 | 2/1998 |
| WO | WO 98/04913 | 2/1998 |
| WO | WO 98/18460 | 5/1998 |
| WO | WO 98/25892 | 6/1998 |
| WO | WO 98/31359 | 7/1998 |
| WO | WO 98/42662 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/06390 | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |
| WO | WO 99/10312 | 3/1999 |
| WO | WO 99/10313 | 3/1999 |
| WO | WO 99/20272 | 4/1999 |
| WO | WO 99/26921 | 6/1999 |
| WO | WO 99/26922 | 6/1999 |
| WO | WO 99/26945 | 6/1999 |
| WO | WO 99/30709 | 6/1999 |
| WO | WO 99/31061 | 6/1999 |
| WO | WO 99/31099 | 6/1999 |
| WO | WO 99/32457 | 7/1999 |
| WO | WO 99/35163 | 7/1999 |
| WO | WO 99/36393 | 7/1999 |
| WO | WO 99/37618 | 7/1999 |
| WO | WO 99/43642 | 9/1999 |
| WO | WO 99/48879 | 9/1999 |
| WO | WO 99/61465 | 12/1999 |
| WO | WO 00/31067 | 6/2000 |
| WO | WO 00/35855 | 6/2000 |

OTHER PUBLICATIONS

Frank, R., et al., "Extremely mild reagent for Boc deprotection," *J. Chem. Commun. (Cambridge)*, 1996, 22, 2509–2510, doc. No. 126:104395 (abstract only, 3 pages).

Kobayashi, A., et al., "Syntheses of 2–dialkylamino–4, 4–disubstituted 5 (4H)–thiazolones," *J. Yakugaku Zasshi*, 1970, 90(11), 1377–1380, doc. No. 74:31713 (abstract only, 3 pages).

Koenig, H.B., et al., ".beta.–Lactam antibiotics," *Ger. Offen.*, 41 pages, doc. No. 83:97276 (abstract only, 5 pages).

Masuda, T., *Jpn. Kodai Tokkyo Koho*, 22 pages, doc. No. 115:280022 (abstract only, 1 page).

Pfeifer, T., et al., "Specific fragmentation of thioxo peptides facilitates the assignment of the thioxylated amino acid," *J. Mass Spectrom*, 1997, 32(10), 1064–1071, doc. No. 127:331738 (abstract only 2 pages).

Sawa, N., et al., "Preparation of 4(5)–thiocarbamoylimidazole compounds," *Jpn. Kokai Tokkyo Koho*, 33 pages, doc. No. 115:183296 (abstract only, 2 pages).

Schutkowski, M., et al., "Inhibition of peptidyl–prolyl cis/trans isomerase activity by substrate analog structures: thioxo tetrapeptide–4–nitroanilides," *Biochemistry*, 1995, 34(40), 13016–13026, doc. No. 123:221511 (abstract only, 4 pages).

"Cephalosporins," *Jpn. Kokai Tokkyo Koho*, 40 pages, doc. No. 99:5433 (abstract only, 2 pages).

Hammadi, A., et al., "Diastereoselective hydrogenation of monodehydro enkephalins controlled by chiral rhodium catalysts," *Tetrahedron: Asymmetry*, 1992, 3(10), XP002106601, 1247–1262.

Nunami, K., et al., "A novel synthesis of methyl 1,5–disubstituted imidazole–4–carboxylates using 3–bromo–2–isocyanoacrylates," *J. Org. Chem.*, 1994, 59, XP002106602, 7635–7642.

Shimohigashi, Y., et al., "Dehydro–enkephalins," *Int. J. Peptide Protein Res.*, 1983, 21, XP002106600, 202–208.

Strange, P.G., et al., "Studies of enzyme–mediated reactions. Part II. Stereochemistry of the elimination of ammonia form L–tyrosine catalysed by the enzyme from maize," *J. Chem. Soc., Perkin I*, 1972, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

Lobb, R.R., et al., "Small molecule antagonists of alpha4 integrins: novel drugs for asthma," *Exp. Opin, Invest. Drugs*, 1999, XP000885957, 8(7), 935–945.

Samanen, J., et al., "Vascular indications for integrin alpha V antagonists," *Current Pharm. Design.*, 1997, 3, 545–584.

Šavrda, J., "CIS–TRANS isomerism of N–ACYL derivatives of proline and its analogues, linear peptides with CIS peptide bonds," *Proc. 14$^{th}$ European Peptide Symposium*, Loffet, A. (ed.), 1976, 653–656.

Azzouny, A. E., et al., "Synthesis of some N–substituted salicylamides structurally related to certain antimicrobials," *Pharmazie*, 1977, 32(6), 318–323 (abstract).

Badshah, A., et al., "Catalytic reduction of azlactones in alkaline media. Synthesis of amino acids," *J. of Organic Chemistry*, 1972, 37(18), 2916–2918.

Tous, G., et al., "O'–(Epoxyalkyl) tyrosines and (Epoxyalkyl) phenylalanine as irreversible inactivators of serine proteases: synthesis and inhibition mechanism," *J. of Medicinal Chemistry*, 1990, 33(6), 1620–1634.

Alhaique, F., et al., "Cyclisation of dinitriles by sodium alkoxides a new synthesis of naphthyridines," *Tetrahedron Letters*, 1975, 3, 173–174.

Ames, D.E., et al., "Condensation of β–dicarbonyl compounds with halogenopyridinecarb–oxylic acids. A convenient synthesis of some napthyridine derivatives," *J.C.S. Perkin I*, 1972, 705–710.

Bodor, N., "Novel approaches in prodrug design," *Alfred Benzon Symposium*, 1982, 17, 156–177.

Brooks, Peter C., et al., "Antiintegrin αvβ3 blocks human breast cancer growth and angiogenesis in human skin," *J. Clin. Invest.*, 1995, 96, 1815–1822.

Koho, *Chemical Abstracts*, "N–[4–Thiazolidinyl)carbonyl] amino acid derivatives," 1981, 95(19), Abstract No. 169173f, 1 page; JP Patent, XP–002114107.

Davies, S..G., et al., "Asymmetric synthesis of R–β–amino butanoic acid and S–β–tyrosine: homochiral lithium amide equivalents for Michael additions toα,β–unsaturated esters," *Tetra. Asymmetry*, 1991, 2(3), 183–186.

Erle, D.J., et al., "Expression and function of the Mad-CAM–1 receptor, integrin α4β7, on human leukocytes," *J. Immunol.*, 1994, 153, 517–528.

Giacomello, et al., "Synthesis of 2,6–napthyridine," *Tetra. Letters*, 1965, 16, 1117–1121.

Hammes, H., et al., "Subcutaneous injection of a cyclic peptide antagonist of vitronectin receptor–type integrins inhibits retinal neovascularization," *Nature Medicine*, 1996, 2, 529–533.

Hodivala–Dilke, K.M., "β3–integrin–deficient mice are a model for glanzmann thrombasthenia showing placental defects and reduced survival," *J. Clin. Invest.*, 1999, 103(2), 229–238.

Kalvin, D.M., et al., Synthesis of (4R)–D,L–[4–$^2$H]– and (4S)–D,L–[4–$^2$H] homoserine lactones, *J. Org. Chem.*, 1985, 50, 2259–2263.

Koivunen, E., et al., "Selection of peptides binding to the α$_5$β$_1$ integrin from phage display library," *J. Biological Chemistry*, 1993, 268(27), 20205–20210.

Mitjans, F., et al., "An anti–αv–integrin antibody that blocks integrin function inhibits the development of a human melanoma in nude mice," *J. Cell Science*, 1995, 108, 2825–2838.

Molina, P., et al., "Iminophosphorane–mediated annelation of a pyridine ring into a preformed pyridine one: synthesis of naphthyridine, pyrido [1,2–c] pyrimidine and pyrido [1,2–c] quinazoline derivatives," *Tetrahedron*, 1992, 48(22), 4601–4616.

Newham, P., et al., "Integrin adhesion receptors: structure, function and implications for biomedicine," *Nolecular Medicine Today*, 1996, 304–313.

Numata, A., et al., "General synthetic method for naphthyridines and their N–oxides containing isoquinolinic nitrogen," *Synthesis*, 1999, 2, 306–311.

Sakamoto, T., et al., "Condensed heteroaromatic ring systems. III. synthesis of naphthyridine derivatives by cyclization of ethynylpyridinecarboxamides," *Chem. Pharm. Bull.* 1985, 33(2), 626–633.

Singh, G., et al., "Prodrug approach in new drug design and development," *J. Sci. Ind. Res.*, 1996, 55, 497–510.

Srivatsa, S.S., et al., "Selective αvβ3 integrin blockade potently limits neointimal hyperplasia and lumen stenosis following deep coronary arterial stent injury: evidence for the functional importance of integrin αvβ3 and osteopontin expression during neointima formation," *Cariovascular Research*, 1997, 36, 408–428.

Stupack, D.G., et al., "induction of α$_v$β$_3$ integrin–mediated attachment to extracellular matrix in β$_1$ integrin (CD29)–negative B cell lines," *Experi. Cell Research*, 1992, 203, 443–448.

Tan R., et al., "Synthesis of 2, 6–naphthyridine and some of its derivatives," *Tetrahedron Letters*, 1965, 31, 2737–2744.

Buckle, D.R., et al., "Non thiazolidinedione Antihyperglycaemic Agents. 1: α–Heteroatom Substituted β–Phenylpropanoic Acids," *Bioorg. Med. Chem. Lett.*, 1996, 6(17), 2121–2126.

Keenan, R.M. et al., "Discovery of Potent Nonpeptide Vitronectin Receptor (avβ$_3$) Antagonists," *J. Med. Chem.*, 1997, 40(15), 2289–2292.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.*, 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.*, 1996, 6(21), 2481–2486.

Ukai, Y. et al., "A novel synthetic inhibitor of endopeptidase–24.15," *Chemical Abstracts*, 1997, 127(2), 1 page.

Venturella, V.S. et al., "Substituted 1,3–Dihydro–4H–furo [3,4–d]–1,3–benzodiazepine–3–ones: Synthesis and Scope of the Method," *J. Heterocyclic Chem.*, 1969, 6(5), 671–679.

Wojciechowsak, H. et al., "Preparation of 2,4–dinitrophenyl derivatives of tyrosine," *Chemical Abstracts*, 1968, 68(25), Abstract No. 11496r, 1 page.

Abraham, W.M. et al., "α$_4$–Integrins Mediate Antigen–Induced Late Bronchial Responses and Prolonged Airway Hyperresponsiveness in Sheep," *J. Clin. Invest.*, 1994, 93, 776–787.

Bach et al., "Anomalous optical rotation and circular dichroism of N–thioacylated.alpha.–amino acids and deriva," *Acta Chem. Scand.*, 1966, 20(10), 2781–2794.

Barrett, G.C., "Circular dichroism of N–thiobenzoly–1–α–amino acids. III. Their circular dichroism through the near–ultraviolet wavelength range," *J. Chem. Soc.*, 1967, Section C, 1–5.

Berlin, C. et al., "α4β7 Integrin Mediates Lymphocyte Binding to the Mucosal Vascular Addressin MAdCAM–1," *Cell*, 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs," *J. Immunol.*, 1996, 157, 4094–4099.

Briskin, M.J. et al., "Structural Requirements for Mucosal Vascular Addressin Binding to Its Lymphocyte Receptor α$_4$β$_7$," *J. Immunol.*, 1996, 156, 719–726.

Cardarelli, P.M. et al., "Cyclic RGD Peptide Inhibits α4β7 Interaction with Connecting Segment 1 and Vascular Cell Adhesion Molecule," *J. Biol. Chem.*, 1994, 269(28), 18668–18673.

*Chemical Abstracts*, "N–[4–Thiazolidinyl)carbonyl]amino acid derivatives," 1981, 95(19), Abstract No. 169173f, 1 page.

Corey, E.J. et al., "A Synthetic Method for Formyl→Ethynyl Conversion (RCHO→RC≡CH or RC≡CR')," *Tetrahedron Lett.*, 1972, 36, 3769–3772.

Cornforth, J.W., "Oxazoles and Oxazolones," *Chem. Penicillin*, Princeton Book Review, 1949, pp. 688, 799, and 800.

Ferguson, T.A. et al., "Two integrin–binding peptides abrogate T cell–mediated immune responses in vivo," *Proc. Natl. Acad. Sci. USA*, 1991, 88, 8072–8076.

Fu, H. et al., "Preliminary study on synthesis and antitumor activity in vitro of derivatives of timonacic," *Chemicals Abstracts*, 1988, 108(17), Abstract No. 150358k, 1 page.

Harris, R.L.N. et al., *Aust. J. Chem.*, "Potential wool growth inhibitors. 2(1H)–Pyridone analogs of mimosine," 1977, 30(3), 649–655.

Hartke, K. et al., "Dithio and thiono esters. Part 61. Synthesis of α–amino dithioesters and endothiodepeptides," *J. Prakt. Chem.*, 1996, 338(3), 251–256.

Holzmann, B. et al., "Peyer's patch–specific lymphocyte homing receptors consist of a VLA–4–like α chain associated with either of two integrin β chains, one of which is novel," *EMBO J.*, 1989, 8(6), 1735–1741.

Humphries, M.J. et al, "Mechanisms of VCAM–1 and fibronectin binding to integrin $\alpha 4\beta 1$ : implications for integrin function and rational drug design," *Ciba Foundation Symposium*, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1," *J. Immunol.*, 1992, 149(10), 3394–3402.

Jaynes, B.H. et al., "Synthesis and In Vivo Antibacterial Activity of Hygromycin a Analogs Modified at the $C_4$' Aryl Position," *Bioorg. Med. Chem. Letts.*, 1993, 3(8), 1531–1536.

Jepson, J.B. et al., "Reactions of $\alpha$–Thioacylamino–acids. Their conversion into Thiazolones and Derivatives Thereof," *J. Chem. Soc.*, 1955, 1791–1797.

Lei, H. et al., "Efficient Synthesis of a Phosphinate Bis–Amino Acid and Its Use in the Construction of Amphiphilic Peptides," *J. Org. Chem.*, 1994, 59, 4206–4210.

Li, Z. et al., "Effect of an anti–Mo1 MAb on ozone–induced airway inflammation and airway hyperresponsiveness in dogs," *Am. J. Physiol.*, 1992, 263(6 Pt 1), L723–726.

Marlin, S.D. et al., "LFA–1 Immunodeficiency Disease," *J. Exp. Med.*, 1986, 164, 855–867.

Masahiko, N., Japanese Patent No. 57–080370 published May 19, 1982, "Alpha–Methylcinnamic Acid Derivative, its Preparation and Antilipemic Agent Containing The Same," *Patent Abstracts of Japan*, 1982, 1 page.

Nagasawa, H.T. et al., "$\beta$–Substituted Cysteines as Sequestering Agents for Ethanol–Derived Acetaldehyde in Vivo," *J. Med. Chem.*, 1987, 30, 1373–1378.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yakugaku Zasshi*, 1959, 79(12), 1514–1518 (English summary included).

Ohki, S. et al., "Synthesis of quinolizine derivatives. V. Studies on Diastereoisomer of Ethyl 3–Quinolizidinecarboxylate," *Chem. Pharm. Bull.*, 1959, 7(6), 708–712.

Osborne, L., "Leukocyte Adhesion to Endothelium in Inflammation," *Cell*, 1990, 62, 3–6.

Osborn, L. et al., "Direct Expression Cloning of Vascular Cell Adhesion Molecule 1, a Cytokine–Induced Endothelial Protein that Binds to Lymphocytes," *Cell*, 1989, 59, 1203–1211.

Podolsky, D.K. et al., "Attenuation of Colitis in the Cotton–top Tamarin by Anti–$\alpha$4 integrin Monoclonal Antibody," *J. Clin. Invest.*, 1993, 92, 372–380.

Schultz, Von O.–E. et al., "Analogos of nuleic acid based as antimetabolites," *Arzneimittel Forschung. Drug Res.*, 1967, 17(8), 1060–1064 (English summary included).

Shroff, H.N. et al., "Small Peptide Inhibitors, of $\alpha_4\beta_7$ Mediated MAdCAM–1 Adhesion to Lymphocytes," *Barge. Med. Chem. Letts.*, 1996, 6(21), 2495–2500.

Sonneberg, A., "Integrins and Their Ligands," *Curr. Topics Microbiol. Immunol.*, 1993, 184, 7–35.

Springer, T.A., "Adhesion receptors of the immune system," *Nature*, 1990, 346, 425–434.

Springer, T.A., "Traffic Signals for Lymphocyte Recirculation and Leukocyte Emigration: The Multistep Paradigm," *Cell*, 1994, 76, 301–314.

Tsunematsu, H. et al., "Hydrolysis of phenylthiazolones of p–guanidinophenylalanine and arginine by trypsin and related enzymes," *J. Biochem.*, 1983, 94(4), 1119–1125.

Vanderslice, P. et al., "A Cyclic Hexapeptide is a Potent Antagonist of $\alpha 4$ Integrins," *J. Immunol.*, 1997, 158, 1710–1718.

Yang, X., "A predominant role of integrin $\alpha 4$ in the spontaneous development of autoimmune diabetes in nonobese diabetic mice," *Proc. Natl. Acad. Sci. USA*, 1994, 91, 12604–12608.

Yednock, T.A., "Prevention of experimental autoimmune encephalomyelitis by antibodies against $\alpha 4\beta 1$ integrin," *Nature*, 1992, 356, 63–66.

Whitlock, B.J. et al., "Structure and synthesis of lathyrine," *J. Org. Chem.*, 1965, 30, 115–118.

WPI/Derwent No. XP–002076854, Japanese Patent No. JP 04 193 895 A (Ajinomoto, K.K.), Jul. 13, 1992, DW9234, 1 Page, Abstract Only.

WPI/Derwent No. XP–002076855, Japanese Patent No. JP 56 049 373 A (Dainippon Pharm Co Ltd), May 2, 1981, DW8125, 1 Page, Abstract Only.

Rico, J.G. et al., "A highly stereoselective michael addition to an $\alpha$, $\beta$–unsaturated ester as the crucial step in the synthesis of a novel $\beta$–amino acid–containing fibrinogen receptor antagonist", *J. Org. Chem*, 1993, vol. 58, pp. 7948–7951.

Zablocki, J.A. et al., "Potent in vitro and in vivo inhibitors of platelet aggregation based upon the Arg–Gly–Asp sequences of fibrinogen", *J. Med. Chem.*, 1995, vol. 38, pp. 2378–2394.

* cited by examiner

PHENYLALKANOIC ACID DERIVATIVES

This invention relates to a series of phenylalkanoic acid derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T A. Nature, 346, 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed α4β1 consists of the integrin alpha 4 chain associated with the integrin beta 1 chain, but is also widely referred to as Very Late Antigen 4 or VLA4. Not all of the potential pairings of integrin, alpha and beta chains have yet been observed in nature and the integrin family has been subdivided into a number of subgroups based on the pairings that have been recognised [Sonnenberg, A. ibid].

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the α4 chain which can pair with two different beta chains β1 and β7 [Sonnenberg, A. ibid]. The α4β1 pairing occurs on many circulating leukocytes (for example lymphocytes, monocytes and eosinophils) although it is absent or only present at low levels on circulating neutrophils. α4β1 binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between α4β1 and ligands on other cells and the extracellular matrix plays an important role in leukocyte migration and activation [Yednock, T. A. et al, Nature, 356, 63, (1992); Podolsky, D. K. et al. J. Clin. Invest. 92, 373, (1993); Abraham, W. M. et al. J. Clin. Invest. 93, 776, (1994)].

The integrin generated by the pairing of α4 and β7 has been termed LPAM-1 [Holzmann, B and Weissman, I. EMBO J. 8, 1735, (1989)] and like α4β1 binds to VCAM-1 and fibronectin. In addition, α4β7 binds to an adhesion molecule believed to be involved in the homing of leukocytes to mucosal tissue termed MAdCAM-1 [Berlin, C. et al, Cell, 74, 185, (1993)]. The interaction between α4β7 and MAdCAM-1 may also be important at sites of inflammation outside of mucosal tissue [Yang, X-D. et al, PNAS, 91, 12604 (1994)].

Regions of the peptide sequence recognised by α4β1 and α4β7 when they bind to their ligands have been identified. α4β1 seems to recognise LDV, IDA or REDV peptide sequences in fibronectin and a QIDSP sequence in VCAM-1 [Humphries, M. J. et al, ibid] whilst α4β7 recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vanderslice, P. J. Immunol. 158, 1710, (1997)]. It has also been reported that a short peptide sequence derived from the α4β1 binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is very important to be able to identify selective inhibitors of the alpha 4 subgroup.

We have now found a group of compounds which are potent and selective inhibitors of α4 integrins. Members of the group are able to inhibit α4 integrins such as α4β1 and/or α4β7 at concentrations at which they generally have no or minimal inhibitory action on a integrins of other subgroups. The compounds are thus of use in medicine, for example in the prophylaxis and treatment of immune or inflammatory disorders as described hereinafter.

Thus according to one aspect of the invention we provide a compound of formula (1)

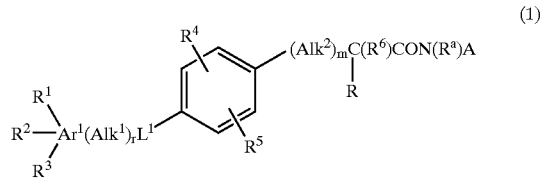

wherein

Ar$^1$ is an aromatic or heteroaromatic group;

R$^1$, R$^2$, R$^3$, R$^4$ and R$^5$ which may be the same or different is each an atom or group —L$^2$(Alk$^3$)$_t$L$^3$(R$^7$)$_u$ in which L$^2$ and L$^3$ which may be the same or different is each a covalent bond or a linker atom or group, t is zero or the integer 1, u is an integer 1, 2 or 3, Alk$^3$ is an aliphatic or heteroaliphatic chain and R$^7$ is a hydrogen or halogen atom or a group selected from alkyl, —OR$^8$ [where R$^8$ is a hydrogen atom or an optionally substituted alkyl group], —SR$^8$, —NR$^8$R$^9$ [where R$^9$ is as just defined for R$^8$ and may be the same or different], —$NO_2$, —CN, —$CO_2R^8$, —$SO_3H$, —$S(O)R^8$, —$SO_2R^8$, —$OCO_2R^8$, —$CONR^8R^9$, —$OCONR^8R^9$, —$CSNR^8R^9$, —$COR^8$, —$OCOR^8$, —$N(R^8)COR^9$, —$N(R^8)CSR^9$, —$SO_2N(R^8)(R^9)$, —$N(R^8)SO_2R^9$, —$N(R^8)CON(R^9)(R^{10})$, [where $R^{10}$ is a hydrogen atom or an optionally substituted alkyl group] —$N(R^8)CSN(R^9)(R^{10})$ or —$N(R^8)SO_2N(R^9)(R^{10})$;

$Alk^1$ is an optionally substituted aliphatic or heteroaliphatic chain;

$L^1$ is a covalent bond or a linker atom or group;

$Alk^2$ is a straight or branched alkylene chain;

m is zero or an integer 1;

$R^6$ is a hydrogen atom or a methyl group;

r is zero or the integer 1;

R is a carboxylic acid (—$CO_2H$) or a derivative thereof;

$R^a$ is a hydrogen atom or a methyl group;

A is an optionally substituted aliphatic, heteroaliphatic, cycloaliphatic, polycycloaliphatic, heterocycloaliphatic, polyheterocycloaliphatic, aromatic or heteroaromatic group;

and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise.

In the compounds of formula (1), derivatives of the carboxylic acid group R include carboxylic acid esters and amides. Particular esters and amides include —$CO_2Alk^5$ and —$CONR^8R^9$ groups as described herein.

In general, the substituents $R^1$, $R^2$ and $R^3$ in compounds of the invention may be positioned on any available carbon atom, or, when present, nitrogen atom in the aromatic or heteroaromatic group represented by $Ar^1$.

When $Alk^1$ and/or the group A is present in compounds of formula (1) as an optionally substituted aliphatic chain it may be an optionally substituted $C_{1-10}$ aliphatic chain. Particular examples include optionally substituted straight or branched chain $C_{1-6}$ alkyl, $C_{2-6}$ alkenyl, or $C_{2-6}$ alkynyl chains.

Heteroaliphatic chains represented by $Alk^1$ and/or the group A include the aliphatic chains just described but with each chain additionally containing one, two, three or four heteroatoms or heteroatom-containing groups. Particular heteroatoms or groups include atoms or groups $L^4$ where $L^4$ is as defined above for $L^1$ when $L^1$ is a linker atom or group. Each $L^4$ atom or group may interrupt the aliphatic chain, or may be positioned at its terminal carbon atom to connect the chain to an adjoining atom or group.

Particular examples of aliphatic chains represented by $Alk^1$ and/or the group A include optionally substituted —$CH_2$—, —$CH_2CH_2$—, —$CH(CH_3)$—, —$C(CH_3)_2$—, —$(CH_2)_2CH_2$—, —$CH(CH_3)CH_2$—, —$(CH_2)_3CH_2$—, —$CH(CH_3)CH_2CH_2$—, —$CH_2CH(CH_3)CH_2$—, —$C(CH_3)_2 CH_2$—, —$(CH_2)_4CH_2$—, —$(CH_2)_5CH_2$—, —CHCH—, —CHCHCH$_2$—, —$CH_2$CHCH—, —CHCHCH$_2$CH$_2$—, —$CH_2$CHCHCH$_2$—, —$(CH_2)_2$CHCH—, —CC—, —CCCH$_2$—, —$CH_2$CC—, —CCCH$_2$CH$_2$—, —$CH_2$CCCH$_2$—, or —$(CH_2)_2$CC— chains. Where appropriate each of said chains may be optionally interrupted by one or two atoms and/or groups $L^4$ to form an optionally substituted heteroaliphatic chain. Particular examples include optionally substituted —$L^4CH_2$—, —$CH_2L^4CH_2$—, —$L^4(CH_2)_2$—, —$CH_2L^4(CH_2)_2$—, —$(CH_2)_2L^4CH_2$—, —$L^4(CH_2)_3$— and —$(CH_2)_2L^4(CH_2)_2$— chains. The substituents which may be present on aliphatic or heteroaliphatic chains represented by $Alk^1$ include one, two, three or more substituents where each substituent may be the same or different and is selected from halogen atoms, e.g. fluorine, chlorine, bromine or iodine atoms, or $C_{1-6}$alkoxy, e.g. methoxy or ethoxy, thiol, $C_{1-6}$alkylthio e.g. methylthio or ethylthio, amino or substituted amino groups. Substituted amino groups include —$NHR^{12}$ and —$N(R^{12})_2$ groups where $R^{12}$ is an optionally substituted straight or branched alkyl group as defined below for $R^{11}$. Where two $R^{12}$ groups are present these may be the same or different. Particular examples of substituted chains represented by $Alk^1$ include those specific chains just described substituted by one, two, or three halogen atoms such as fluorine atoms, for example chains of the type —$CH(CF_3)$—, —$C(CF_3)_2$— —$CH_2CH(CF_3)$—, —$CH_2C(CF_3)_2$—, —$CH(CF_3)$— and —$C(CF_3)_2 CH_2$—.

$Alk^2$ in the compounds of the invention may be for example a straight or branched $C_{1-3}$alkylene chain. Particular examples include —$CH_2$—, —$CH(CH_3)$— and —$(CH_2)_2$—.

When in the compounds of formula (1) $L^1$, $L^2$ and/or $L^3$ is present as a linker atom or group it may be any divalent linking atom or group. Particular examples include —O— or —S— atoms or —C(O)—, —C(O)O—, —OC(O)—, —C(S)—, —S(O)—, —S(O)$_2$—, —$N(R^{11})$— [where $R^{11}$ is a hydrogen atom or an optionally substituted alkyl group], —$CON(R^{11})$—, —$OC(O)N(R^{11})$—, —$CSN(R^{11})$—, —$N(R^{11})CO$—, —$N(R^{11})C(O)O$—, —$N(R^{11})CS$—, —$S(O)_2N(R^{11})$—, —$N(R^{11})S(O)_2$—, —$N(R^{11})CON(R^{11})$, —$N(R^{11})CSN(R^{11})$—, or —$N(R^{11})SO_2N(R^{11})$— groups. Where the linker group contains two $R^{11}$ substituents, these may be the same or different.

When $R^7$, $R^8$, $R^9$, $R^{10}$ and/or $R^{11}$ in the compounds of formula (1) is an alkyl group it may be a straight or branched $C_{1-6}$alkyl group, e.g. a $C_{1-3}$alkyl group such as a methyl or ethyl group. Optional substituents which may be present on such groups include for example one, two or three substituents which may be the same or different selected from halogen atoms, for example fluorine, chlorine, bromine or iodine atoms, or hydroxy or $C_{1-6}$alkoxy e.g. methoxy or ethoxy groups.

When $Alk^3$ is present in the compounds of formula (1) as an aliphatic or heteroaliphatic chain it may be for example any of the above-mentioned $C_{1-10}$aliphatic or heteroaliphatic chains described for $Alk^1$.

Halogen atoms represented by $R^7$ in compounds of the invention include fluorine, chlorine, bromine, or iodine atoms.

Examples of the substituents represented by $R^1$, $R^2$, $R^3$, $R^4$ and $R^5$ in compounds of formula (1) include atoms or groups —$L^2Ak^3L^3R^7$, —$L^2Alk^3R^7$, —$L^2R^7$ and -$Alk^3R^7$ wherein $L^2$, $Alk^3$, $L^3$ and $R^7$ are as de above. Particular examples of such substituents include —$L^2CH_2L^3R^7$, —$L^2CH(CH_3)L^3R^7$, —$L^2CH(CH_2)_2L^3R^7$, —$L^2CH_2R^7$, —$L^2CH(CH_3)R^7$, —$L^2(CH_2)_2R^7$, —$CH_2R^7$, —$CH(CH_3)R^7$, $(CH_2)_2R^7$ and —$R^7$ groups.

Thus each of $R^1$, $R^2$, $R^3$, $R^4$ and $R^5$ in compounds of the invention may be for example a hydrogen atom, a halogen atom, e.g. a fluorine, chlorine, bromine or iodine atom, or a $C_{1-6}$alkyl, e.g. methyl, ethyl, n-propyl, i-propyl, n-butyl or t-butyl, $C_{1-6}$alkylamino, e.g. methylamino or ethylamino, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, halo$C_{1-6}$alkyl, e.g. trifluoromethyl, halo$C_{1-6}$alkoxy, e.g. trifluoromethoxy, $C_{1-6}$alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$ alkoxy, e.g. methylaminoethoxy, $C_{1-6}$dialkylamino$C_{1-6}$ alkoxy, e.g. dimethylaminoethoxy, diethylaminoethoxy, isopropylaminoethoxy, or dimethylaminopropoxy, nitro, cyano, amidino, hydroxyl (—OH), formyl [HC(O)—], carboxyl (—$CO_2H$), —$CO_2Alk^5$ [where $Alk^5$ is as defined below], $C_{1-6}$ alkanoyl e.g. acetyl, thiol (—SH), thio$C_{1-6}$alkyl, e.g. thiomethyl or thioethyl, sulphonyl (—$SO_3H$), $C_{1-6}$alkylsulphinyl e.g. methylsulphinyl, $C_{1-6}$alkylsulphonyl, e.g. methylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$ alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, amino$C_{1-6}$ alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino group.

Optionally substituted cycloaliphatic groups represented by the group A in compounds of the invention include optionally substituted $C_{3-10}$ cycloaliphatic groups. Particular examples include optionally substituted $C_{3-10}$cycloalkyl, e.g. $C_{3-7}$cycloalkyl or $C_{3-10}$cycloalkenyl, e.g $C_{3-7}$cycloalkenylgroups.

Optionally substituted heterocycloaliphatic groups represented by the group A include optionally substituted $C_{3-10}$heterocycloaliphatic groups. Particular examples include optionally substituted $C_{3-10}$heterocycloalkyl, e.g. $C_{3-7}$heterocycloalkyl, or $C_{3-10}$heterocycloalkenyl, e.g. $C_{3-7}$hetercycloalkenyl groups, each of said groups containing one, two, three or four heteroatoms or heteroatom-containing groups $L^4$ as defined above.

Optionally substituted polycycloaliphatic groups represented by the group A include optionally substituted $C_{7-10}$ bi- or tricycloalkyl or $C_{7-10}$bi- or tricycloalkenyl groups. Optionally substituted polyheterocycloaliphatic groups represented by the group A include the optionally substituted polycycloalkyl groups just described, but with each group additionally containing one, two, three or four $L^4$ atoms or groups.

Particular examples of cycloaliphatic, polycycloaliphatic, heterocycloaliphatic and polyheterocycloaliphatic groups represented by the group A include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the $R^1$ and $R^6$ cycloaliphatic, polycycloaliphatic, heterocycloaliphatic or polyheterocycloaliphatic groups represented by the group A include one, two, three or more substituents each selected from halogen atoms, e.g. fluorine, chlorine, bromine or iodine atoms, or $C_{1-6}$alkyl, e.g. methyl or ethyl, halo$C_{1-6}$alkyl, e.g. halomethyl or haloethyl such as difluoromethyl or trifluoromethyl, optionally substituted by hydroxyl, e.g. —$C(OH)(CF_3)_2$, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, $C_{1-6}$alkylthio e.g. methylthio or ethylthio, or -$(Alk)_vR^{12}$ groups in which Alk is a straight or branched $C_{1-3}$alkylene chain, v is zero or an integer 1 and $R^{12}$ is a —OH, —SH, —$N(R^{11a})_2$, —CN, —$CO_2R^{11a}$, —$NO_2$, —$CON(R^{11a})_2$, —$CSN(R^{11a})_2$, —$COR^{11a}$, —$CSN(R^{11a})_2$, —$N(R^{11a})COR^{11a}$, —$N(R^{11a})CSR^{11a}$, —$SO_2N(R^{11a})_2$, —$N(R^{11a})SO_2R^{11a}$, —$N(R^{11a})CON(R^{11a})_2$, —$N(R^{11a})CSN(R^{11a})$ or —$N(R^{11a})SO_2N(R^{11a})_2$ group in which $R^{11a}$ is an atom or group as defined herein for $R^{11}$. Additionally, when the group A is a heterocyclo-aliphatic group containing one or more nitrogen atoms each nitrogen atom may be optionally substituted by a group —$(L^5)_p(Alk^6)_qR^{15}$ in which $L^5$ is —C(O)—, —C(O)O—, —C(S)—, —$S(O)_2$—, —$CON(R^{11})$—, —$CSN(R^{11})$—, —$SON(R^{11})$— or $SO_2N(R^{11})$—; p is zero or an integer 1; $Alk^6$ is an optionally substituted aliphatic or heteroaliphatic chain; q is zero or an integer 1; and $R^{15}$ is a hydrogen atom or an optionally substituted cycloaliphatic, heterocycloaliphatic, polycycloaliphatic, polyheterocycloaliphatic, aromatic or heteroaromatic group.

Optionally substituted aliphatic or heteroaliphatic chains represented by $Alk^6$ include those optionally substituted chains described above for $Alk^1$.

Cycloaliphatic, heterocycloaliphatic, polycycloaliphatic or polyheterocycloaliphatic groups represented by $R^{15}$ include those groups just described for the group A. Optional substituents which may be present on these groups include those described above in relation to $Alk^1$ aliphatic and heteroaliphatic chains.

Aromatic groups represented by the group $Ar^1$ and/or A in compounds of the invention include for example monocyclic or bicyclic fused ring $C_{6-12}$ aromatic groups, such as phenyl, 1- or 2-naphthyl, 1- or 2-tetrahydronaphthyl, indanyl or indenyl groups. Aromatic groups represented by the group A may be optionally substituted by one, two, three or more $R^{13}$ atoms or groups as defined below.

Heteroaromatic groups represented by the group $Ar^1$ and/or A in the compounds of formula (1) include for example $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—$C_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, qunoxalinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on the aromatic or heteroaromatic groups represented by the group A include one, two, three or more substituents, each selected from an atom or group $R^{13}$ in which $R^{13}$ is —$R^{13a}$ or -$Alk^4(R^{13a})_m$, where $R^{13a}$ is a halogen atom, or an amino (—$NH_2$), substituted amino, nitro, cyano, amidino, hydroxyl (—OH), substituted hydroxyl, formyl, carboxyl (—$CO_2H$), esterified carboxyl, thiol (—SH), substituted thiol, —$COR^{14}$ [where $R^{14}$ is an -$Alk^3(R^{13a})_m$, aryl or heteroaryl group], —$CSR^{14}$, —$SO_3H$, —$SO_2R^{14}$ —$SO_2NH_2$, —$SO_2NHR^{14}$ $SO_2N(R^{14})_2$, —$CONH_2$, —$CSNH_2$, —$CONHR^{14}$, —$CSNHR^{14}$, —$CON[R^{14}]_2$, —$CSN(R^{14})_2$, —$N(R^{11})SO_2R^{14}$, —$N(SO_2R^{14})_2$, —$NH(R^{11})SO_2NH_2$, —$N(R^{11})SO_2NHR^{14}$, —$N(R^{11})SO_2N(R^{14})_2$, —$N(R^{11})$ $COR^{14}$, —$N(R^{11})CONH_2$, —$N(R^{11})CONHR^{14}$, —$N(R^{11})$ $CON(R^{14})_2$, —$N(R^{11})CSNH_2$, —$N(R^{11})CSNHR^{14}$, —$N(R^{11})CSN(R^{14})_2$, —$N(R^{11})CSR^{14}$, —$N(R^{11})C(O)OR^{14}$, —$SO_2NHet^1$ [where —$NHet^1$ is an optionally substituted $C_{5-7}$cyclicamino group optionally containing one or more other —O— or —S— atoms or —$N(R^{11})$—, —C(O)— or —C(S)— groups], —$CONHet^1$, —$CSNHet^1$, —$N(R^{11})$ $SO_2NHet^1$, —$N(R^{11})CONHet^1$, —$N(R^{11})CSNHet^1$, —$SO_2N(R^{11})Het^2$ [where $Het^2$ is an optionally substituted monocyclic $C_{5-7}$carbocyclic group optionally containing one or more —O— or —S— atoms or —$N(R^{11})$—, —C(O)— or —C(S)— groups], -$Het^2$, —$CON(R^{11})Het^2$, —$CSN(R^{11})Het^2$, —$N(R^{11})CON(R^{11})Het^2$, —$N(R^{11})CSN$ ($R^{11})Het^2$, aryl or heteroaryl group; $Alk^4$ is a straight or branched $C_{1-6}$alkylene, $C_{2-6}$alkenylene or $C_{2-6}$alkynylene chain, optionally interrupted by one, two or three —O— or —S— atoms or —$S(O)_n$ [where n is an integer 1 or 2] or —$N(R^{15})$— groups [where $R^{15}$ is a hydrogen atom or $C_{1-6}$alkyl, e.g. methyl or ethyl group]; and m is zero or an integer 1, 2 or 3. It will be appreciated that when two $R^{11}$ or $R^{14}$ groups are present in one of the above substituents, the $R^{11}$ or $R^{14}$ groups may be the same or different.

When in the group -$Alk^4(R^{13a})_m$, m is an integer 1, 2 or 3, it is to be understood that the substituent or substituents $R^{13a}$ may be present on any suitable carbon atom in -$Alk^4$. Where more than one $R^{13a}$ substituent is present these may be the same or different and may be present on the same or different atom in -$Alk^4$. Clearly, when m is zero and no substituent $R^{13a}$ is present the alkylene, alkenylene or alkynylene chain represented by $Alk^4$ becomes an alkyl, alkenyl or alkynyl group.

When $R^{13a}$ is a substituted amino group it may be for example a group —$NHR^{14}$ [where $R^{14}$ is as defined above] or a group —$N(R^{14})_2$ wherein each $R^{14}$ group is the same or different.

When $R^{13a}$ is a halogen atom it may be for example a fluorine, chlorine, bromine, or iodine atom.

When $R^{13a}$ is a substituted hydroxyl or substituted thiol group it may be for example a group —$OR^{14}$ or a —$SR^{14}$ or —$SC(=NH)NH_2$ group respectively.

Esterified carboxyl groups represented by the group $R^{13a}$ include groups of formula —$CO_2Alk^5$ wherein $Alk^5$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^5$ group include $R^{13a}$ substituents described above.

When $Alk^4$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —$S(O)$—, —$S(O)_2$— or—$N(R^{12})$— groups.

Aryl or heteroaryl groups represented by the groups $R^{13a}$ or $R^{14}$ include mono- or bicyclic optionally substituted $C_{6-12}$ aromatic or $C_{1-9}$ heteroaromatic groups as described above for the group $Ar^2$. The aromatic and heteroaromatic groups may be attached to the remainder of the compound of formula (1) by any carbon or hetero e.g. nitrogen atom as appropriate.

When —$NHet^1$ or -$Het^2$ forms part of a substituent $R^{13}$ each may be for example an optionally substituted pyrrolidinyl, pyrazolidinyl, piperazinyl, morpholinyl, thiomorpholinyl, piperidinyl or thiazolidinyl group. Additionally $Het^2$ may represent for example, an optionally substituted cyclopentyl or cyclohexyl group. Optional substituents which may be present on —$NHet^1$ or -$Het^2$ include those $R^7$ substituents described above.

Particularly useful atoms or groups represented by $R^{13}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, or thienyl, morpholinyl, thiomorpholinyl, piperazinyl, pyrrolidinyl, piperadinyl, $C_{1-6}$alkylamino, e.g. methylamino or ethylamino, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy, ethoxy or propoxy, hydroxy$C_{1-6}$alkoxy, e.g. 2-hydroxyethoxy, optionally substituted phenoxy, pyridyloxy, thiazolyoxy, phenylthio or pyridylthio, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino or ethylamino, optionally substituted $C_{6-12}$aryl$C_{1-6}$alkylamino e.g. benzylamino, amino (—$NH_2$), amino$C_{1-6}$alkylamino e.g. aminomethylamino, aminoethylamino or aminopropylamino, amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, hydroxy$C_{1-6}$alkylamino, e.g. hydroxymethylamino or hydroxyethylamino, $Het^1NC_{1-6}$ alkylamino e.g. morpholinopropylamino or piperidinylethylamino, imido, such as phthalimido or naphthalimido, e.g. 1,8-naphthalimido, nitro, cyano, amidino, hydroxyl (—OH), formyl [HC(O)—], carboxyl (—$CO_2H$), —$CO_2Alk^5$ [where $Alk^5$ is as defined above], $C_{1-6}$ alkanoyl e.g. acetyl, optionally substituted benzoyl, thiol (—SH), thio$C_{1-6}$alkyl, e.g. thiomethyl, thioethyl or thiopropyl, thio$C_{1-6}$alkyl$C_{6-12}$aryl e.g. thiobenzyl, —SC(=NH)$NH_2$, sulphonyl (—$SO_3H$), $C_{1-6}$alkylsulphinyl e.g. methylsulphinyl, ethylsulphinyl or propylsulphinyl, $C_{1-6}$alkylsulphonyl, e.g. methylsulphonyl, ethylsulphonyl or propylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$ alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)$NH_2$, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$ alkanoylamino$C_{1-6}$ alkyl, e.g. acetylaminomethyl, $C_{1-6}$alkanoylamino$C_{1-6}$ alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, benzothio, pyridylmethylthio or thiazolylmethylthio groups.

Where desired, two $R^{13}$ substituents may be linked together to form a cyclic group such as a cyclic ether, e.g. a $C_{1-6}$alkylenedioxy group such as methylenedioxy or ethylenedioxy.

It will be appreciated that where two or more $R^{13}$ substituents are present, these need not necessarily be the same atoms and/or groups. In general, the substituent(s) may be present at any available ring position in the aromatic or heteroaromatic group represented by $Ar^2$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds according to the invention the group $Ar^1$ is preferably a phenyl or monocyclic heteroaromatic group. Particularly useful groups of this type are five- or six-membered heteroaromatic groups as described previously, especially five- or six-membered heteroaromatic groups containing one or two heteroatoms selected from oxygen, sulphur or nitrogen atoms. Nitrogen-containing groups are especially useful, particularly pyridyl or pyrimidinyl groups. $R^1$, $R^2$ and $R^3$ attached to these $Ar^1$ groups may each be a hydrogen atom or one of the other atoms or groups generally and particularly described above in relation to $R^1$, $R^2$ and $R^3$. Particularly useful atoms or groups include halogen atoms or alkyl, —$OR^8$, —$SR^8$, $NR^8R^9$, —$NO_2$ or —CN groups as described above in relation to the compounds of formula (1).

A particularly useful group of compounds according to the invention has the formula (2):

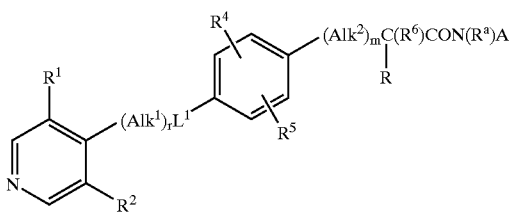

(2)

wherein $R^1$ and $R^2$, which may be the same or different is each an atom or group —$L^2(Alk^3)_tL^3(R^7)_u$ in which $L^2$, $Alk^3$, $t$, $L^3$, $R^7$ and $u$ are as defined for formula (1) provided that $R^1$ and $R^2$ are not both hydrogen atoms;

$Alk^1$, $Alk^2$, m, r, $L^1$, $R^4$, $R^5$, $R^6$, $R^a$, A and R are as defined for formula (1);

and the salts, solvates, hydrates and N-oxides thereof.

$R^1$ and $R^2$ in compounds of formula (2) and in general in compounds of formula (1) is each preferably as particularly described above for compounds of formula (1), other than a hydrogen atom. Particularly useful $R^1$ and $R^2$ substituents include halogen atoms, especially fluorine or chlorine atoms, or methyl, halomethyl, especially —$CF_3$, —$CHF_2$ or —$CH_2F$, methoxy or halomethoxy, especially —$OCF_3$, —$OCHF_2$ or —$OCH_2F$ groups.

$R^3$ in compounds of the invention is in particular a hydrogen atom.

R in the compounds of formulae (1) and (2) is preferably a —$CO_2H$ group.

When present, the aliphatic chain represented by $Alk^1$ in compounds of formulae (1) and (2) is preferably a —$CH_2$— chain.

In general in compounds of formulae (1) and (2) -$(Alk^1)_r$ $L^1$— is preferably —$CH_2O$— or —$CON(R^{11})$—.

In compounds of formulae (1) and (2) m is preferably 1 and $Alk^2$ is preferably —$CH_2$—.

$R^4$ and $R^5$ in the compounds of formulae (1) and (2) may be the same or different and is each preferably a hydrogen or halogen atom or an alkyl, alkoxy, hydroxy, nitro, cyano or —$NR^8R^9$ group.

$R^6$ and $R^a$ in the compounds of formulae (1) and (2) is each preferably a hydrogen atom.

In general in compounds of formulae (1) and (2) the group A may especially be an optionally substituted cycloaliphatic, heterocycloaliphatic, aromatic or heteroaromatic group as defined herein. Particularly useful groups of this type include optionally substituted $C_{5-7}$heterocycloaliphatic, especially optionally substituted pyrrolidinyl or thiazolidinyl, optionally substituted phenyl and optionally substituted $C_{5-7}$heteroaromatic, especially optionally substituted pyridyl groups. Optional substituents on these groups include in particular $R^{13}$ atoms or groups where the group is an aromatic or heteroaromatic group and —$(L^5)_p(Alk^6)_qR^{15}$ groups as described earlier where the group is a nitrogen-containing heterocycloaliphatic group such as a pyrrolidinyl or thiazolidinyl group.

Especially useful A groups include optionally sustituted phenyl or pyridyl groups.

Particularly useful $R^{13}$ substituents in compounds of the invention include a halogen atom, especially fluorine or chlorine, optionally substituted morpholinyl, optionally substituted thiomorpholinyl, optionally substituted piperidinyl, optionally substituted pyrrolidinyl, optionally substituted piperazinyl, thio$C_{1-6}$alkyl, especially thiomethyl, thioethyl or thiopropyl, optionally substituted thiobenzyl, halo$C_{1-6}$alkyl, especially trifluoromethyl, $C_{1-6}$alkyloxy, especially methoxy, ethoxy or propoxy, optionally substituted benzyloxy, halo$C_{1-6}$alkoxy, especially trifluoromethoxy and difluoromethoxy, $C_{1-6}$alkylamino, especially propylamino, $C_{1-6}$dialkylamino, especially dimethylamino or diethylamino, optionally substituted $C_{6-12}$aryl$C_{1-6}$alkylamino, amino$C_{1-6}$alkylamino, especially 3-aminopropylamino, $Het^1NC_{1-6}$alkylamino, especially 3-morpholiopropylamino, optionally substituted phenoxy, hydroxy$C_{1-6}$alkylamino, nitro, carboxyl, —$CO_2Alk^5$ [where $R^5$ is as defined above], especially carboxymethyl and carbonyethyl, carboxamido, $C_{1-6}$alkylaminocarbonyl, $C_{1-6}$dialkylaminocarbonyl, $C_{1-6}$alkanoyl, optionally substituted benzoyl, $C_{1-6}$alkylsulphinyl, $C_{1-6}$alkylsulphonyl, $C_{1-6}$alkylaminosulphonyoyl, $C_{1-6}$dialkylaminosulphonyl, $C_{1-6}$alkylamino-carbonyl and $C_{1-6}$dialkylaminocarbonyl.

Particularly useful —$(L^5)_p(Alk^6)_qR^{15}$ groups include those in which $L^5$ is a —CO— group. $Alk^6$ in these groups is preferably present (i.e. q is preferably an integer 1) and in particular is a —$CH_2$-chain. Compounds of this type in which $R^{15}$ is a hydrogen atom or an optionally substituted aromatic or heteroaromatic group, especially an optionally substituted phenyl, pyridyl or imidazolyl group are particularly preferred. Particularly useful optional substituents on these groups include those $R^{13}$ groups just mentioned.

Particularly useful compounds according to the invention include:

3-(2,6-Dichloroanilino)-2-{4-[(3,5-dichloroisonicotinoyl)amino]benzyl}-3-oxopropanoic acid;

3-(2,6-Dimethoxyanilino)-2-{4-[(3,5-dichloroisonicotinoyl)amino]benzyl}-3-oxopropanoic acid;

2-{4-[3,5-Dichloroisonicotinoyl)amino]benzyl}-3-[(3,5-dichloro-4-pyridinyl)amino]-3-oxapropanoic acid;

2-{4-[(2,6-Dichlorobenzoyl)amino]benzyl}3-(2,6-dimethoxyanilino)-3-oxopropanoic acid;

2-{4-[(2,6-Dichlorobenzyl)oxy]benzyl}3-(2,6-dimethoxyanilino)-3-oxopropanoic acid;

and the salts, solvates, hydrates and N-oxides thereof.

Compounds according to the invention are potent and selective inhibitors of α4 integrins. The ability of the compounds to act in this way may be simply determined by employing tests such as those described in the Examples hereinafter.

The compounds are of use in modulating cell adhesion and in particular are of use in the prophylaxis and treatment of diseases or disorders involving inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1$—$R^6$, $Ar^1$, $L^1$, $Alk^1$, $Alk^2$, m, r, A, $R^a$ and R when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which R is a —$CO_2H$ group may be obtained by hydrolysis of an ester of formula (3):

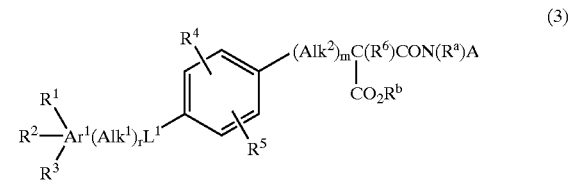

where $R^b$ is an alkyl group, for example a $C_{1-6}$alkyl group as described above.

The hydrolysis may be performed using either an acid or a base depending on the nature of $R^b$, for example an organic acid such as trifluoroacetic acid or an inorganic base such as lithium or potassium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (3) may be prepared by coupling an acid of formula (4):

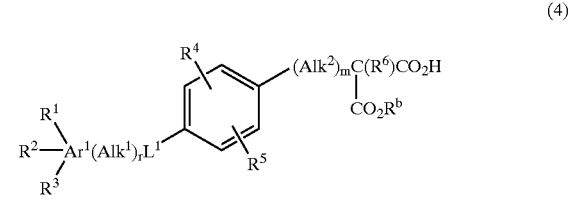

or an active derivative thereof with an amine $ANHR^a$. Active derivatives of acids of formula (4) include anhydrides, esters and halides and may be obtained by standard procedures and may be obtained by standard procedures, for example as described in the Examples hereinafter.

The coupling reaction may be performed using standard conditions for reactions of this type. Thus for example the reaction may be carried out with an active derivative of the acid of formula (4) in the presence of a base, e.g. an organic base such as an amine, e.g. triethylamine or N,N-diisopropylethylamine, or a cyclic amine, such as N-methylmorpholine, or a hydride, such as sodium hydride in an inert organic solvent such as an amide, e.g. a substituted amide such as dimethylformamide, an ether, e.g. a cyclic ether such as tetrahydrofuran or a halogenated hydrocarbon, such as dichloromethane, at a low temperature, e.g. around −30° C. to around ambient temperature.

Where an acid of formula (4) is used, the reaction may additionally be performed in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively, the acid may be reacted with a chloroformate, for example ethylchloroformate, prior to reaction with the amine $ANHR^a$.

The acids of formula (4) may be obtained from simpler, known compounds by one or more standard synthetic methods employing substitution, oxidation, reduction or cleavage reactions as described below and in the Examples hereinafter. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2) where appropriate functional groups exist in these compounds. Additionally, although a number of the intermediate amines $ANHR^a$ for use in the coupling reaction described above are known, others can be derived therefrom using these standard synthetic methods.

Thus compounds of the invention and intermediates thereto may be prepared by alkylation, arylation or heteroarylation. For example, compounds containing a —$L^1$H, —$L^2$H, or —$L^3$H group (where $L^1$, $L^2$ and $L^3$ is each a linker atom or group) may be treated with an alkylating agent:

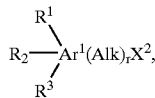

$(R^7)_aL^3Alk^3_rX^2$ or $R^{7a}X^2$ respectively in which $X^2$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group, and $R^{7a}$ is an alkyl group.

The reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran.

In another example, compounds containing a —$L^1$H, —$L^2$H or—$L^3$H group as defined above may be functionalised by acylation or thioacylation, for example by reaction with one of the alkylating agents just described but in which $X^2$ is replaced by a —C(O)$X^3$, C(S)X3, —N($R^8$)CO$X^3$ or —N($R^8$)C(S)$X^3$ group in which $X^3$ is a leaving atom or group as described for $X^2$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation or thioacylation may be carried out under the same conditions with an acid or thioacid (for example one of the alkylating agents described above in which $X^2$ is replaced by a —CO$_2$H or —COSH group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction.

In a further example compounds may be obtained by sulphonylation of a compound containing an —OH group by reaction with one of the above alkylating agents but in which $X^2$ is replaced by a —S(O)Hal or —SO$_2$Hal group in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a —$L^1$H, —$L^2$H or —$L^3$H group as defined above may be coupled with one of the alkylation agents just described but in which $X^2$ is replaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —CO$_2R^8$ or —CO$_2$Alk$^5$ in the compounds may be converted to the corresponding acid [—CO$_2$H] by acid- or base-catalysed hydrolysis depending on the nature of the groups $R^8$ or Alk$^5$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a further example, —OR$^8$ or —OR$^{14}$ groups [where $R^8$ or $R^{14}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —OCH$_2R^{14}$ group (where $R^{14}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [—CO$_2$Alk$^5$ or CO$_2R^8$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —OR$^8$ group by coupling with a reagent $R^8$OH in a solvent such as tetrahydrofuran in the presence of a phosphine, e.g. triphenylphosphine and an activator such as diethyl-, diisopropyl-, or dimethylazodicarboxylate.

Aminosulphonylamino [—NHSO$_2$NH$_2$] groups in the compounds may be obtained, in another example, by reaction of a corresponding amine [—NH$_2$] with sulphamide in the presence of an organic base such as pyridine at an elevated temperature, e.g. the reflux temperature.

In a further example amine (—NH$_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—NH$_2$] groups in compounds of formula (1) may be obtained by hydrolysis from a corresponding imide by reaction with hydrazine in a solvent such as an alcohol, e.g. ethanol at ambient temperature.

In another example, a nitro [—NO$_2$] group may be reduced to an amine [—NH$_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyidisulphide as the electrophile.

In another example, sulphur atoms in the compounds, for example when present in a linker group L$^1$, L$^2$ or L$^3$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suit able solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystalliation and other conventional separation procedures may also be used with intermediates or final products where it is desired to obtain a particular geometric isomer of the invention.

The following Examples illustrate the invention. All temperatures are in ° C. The following abbreviations are used:

| | |
|---|---|
| NMM - N-methylmorpholine; | EtOAc - ethyl acetate; |
| MeOH - methanol; | BOC - butoxycarbonyl; |
| DCM - dichloromethane; | AcOH - acetic acid; |
| DMF - dimethylformamide; | Ar - aryl; |
| Me - methyl; | Et$_2$O - diethyl ether; |
| THF - tetrahydrofuran; | EtOH - ethanol; |
| DMSO - dimethylsulphoxide; | |
| All NMR's were obtained at 300 MHz. | |

INTERMEDIATE 1

{4-[(2,6-Dichlorobenzyl)oxy]phenyl}methanol

A solution of 4-(hydroxymethyl)phenol (38.0 g, 0.31 mmol) and 2,6-dichlorobenzyl bromide (73.4 g, 0.31 mmol) in DMF (500 ml) was treated with caesium carbonate (100 g, 0.31 mmol) and heated to 60° for 16 h. The mixture was cooled to room temperature and the solvent evaporated in vacuo. The residue was partitioned between EtOAc (250 ml) and water (250 ml), the aqueous layer was separated and extracted with EtOAc (250 ml) and the combined organic layers washed with 10% hydrochloric acid (100 ml), NaHCO$_3$ solution (100 ml) and brine (200 ml), dried (MgSO$_4$) and the solvent evaporated in vacuo to give the title compound as a brown oil (88.4 g) which was used without further purification. δH (CDCl$_3$) 7.38–7.21 (5H, m, ArH), 7.02 (2H, d, J 8.7 Hz, ArH), 5.28 (2H, s, CH$_2$OAr) and 4.63 (2H, s, CH$_2$OH).

INTERMEDIATE 2

4-(Bromomethyl)phenyl(2,6-dichlorobenzyl)ether

Thionyl bromide (78 g, 0.38 mmol) was added dropwise to an ice cold solution of Intermediate 1 (88.4 g, 0.31 mmol), in toluene (500 ml). On completion of addition the reaction was warmed to room temperature and stirred for 2 h, then washed with water (200 ml). The aqueous washings were extracted with Et$_2$O (2×200 ml) and the combined organic layers washed with water (200 ml), and NaHCO$_3$ solution (3×200 ml), dried (MgSO$_4$) and the solvent evaporated in vacuo to give a brown oil that was recrystallised from hexane to give the title compound (73.8 g, 69%) as white crystals. δH (CDCl$_3$) 7.36 (4H, m, Ar—H), 7.25 (1H, m, Ar—H), 6.98 (2H, d, J 8.7 Hz), 5.27 (2H, s, CH$_2$OAr) and 4.51 (2H, s, CH$_2$Br).

INTERMEDIATE 3

Dimethyl 2-{4-[(2,6-Dichlorobenzyl)oxy] benzyl}malonate

Sodium metal (1.83 g, 80 mmol) was added to MeOH (100 ml) and stirred until dissolved. Dimethyl malonate (9.55 g, 72.5 mmol) was added to this solution dropwise and the reaction stirred for 20 mins. A solution of the compound of Intermediate 2 (25.0 g, 72.5 mmol) in THF (200 ml) was added by cannula over a period of 1.5 h. The reaction was stirred for 1 h on completion of the addition and quenched with water (100 ml). The mixture was concentrated in vacuo and partitioned between Et$_2$O (200 ml) and water (100 ml). The aqueous layer was separated, extracted with Et$_2$O (200 ml) and the combined organic layers washed with brine (200 ml), dried (MgSO$_4$), and the solvent evaporated in vacuo to give a brown gum (28.6 g).

8 g of this material was triturated with boiling EtOH (100 ml) and the resulting solid removed by filtration. The filtrate was cooled and the solid removed by filtration. The filtrate was concentrated in vacuo to give the title compound as a white solid (3 g). δH (CDCl$_3$) 7.38–7.23 (3H, m, ArH), 7.14 (2H, d, J 8.7 Hz, Ar—H), 6.94 (2H, d, J 8.7 Hz, Ar—H), 5.24 (2H, s, CH$_2$OAr), 3.71 (6H, s, CO$_2$Me), 3.65 (1H, t, J 7.8 Hz, CHCH$_2$) and 3.19 (2H, d, J 7.8 Hz CHCH$_2$).

INTERMEDIATE 4

2-{4-[2,6-Dichlorobenzyl)oxy]benzyl}-3-methoxy-3-oxopropanoic Acid

A solution of Intermediate 3 (3.26 g, 8.2 mmol) in THF (35 ml) and water (10 ml) was treated with LiOH. H$_2$O (0.34 g, 8.2 mmol) and stirred at room temperature for 4 h. The reaction was acidified to pH1 with 10% hydrochloric acid and partitioned between water (10 ml) and DCM (50 ml). The aqueous layer was extracted with DCM (2×50 ml) and the combined organic layers dried (MgSO$_4$) and the solvent evaporated in vacuo to give a brown oil that was purified by chromatography (SiO$_2$, DCM/MeOH 9:1), to give the title compound as a gummy solid, (1.95 g, 62%). δH (CDCl$_3$) 7.36–7.22 (3H, m, Ar—H), 7.15 (2H, d, J 8.6 Hz, Ar—H), 6.93 (2H, d, J 8.6 Hz, Ar—H), 5.22 (2H, s, CH$_2$OAr), 3.67 (3H, s, CO$_2$Me), 3.66 (1H, m, CHCH$_2$) and 3.20 (2H, d, J 7.6 Hz CHCH$_2$).

INTERMEDIATE 5

Methyl 3-Chloro-2-{4-[(2,6-dichlorobenzyl)oxy]benzyl}-3-oxopropanoate

Thionyl chloride (3.0 g, 25.5 mmol) was added to a solution of Intermediate 4 (1.95 g, 5.1 mmol) in DCM (20 ml) containing 1 drop of DMF. The reaction was stirred at room temperature for 16 h then concentrated in vacuo to give the title compound as a gum, (2.0 g), which was used without further purification.

INTERMEDIATE 6

Diethyl-2-(4-nitrobenzyl)malonate

Diethyl malonate (7.41 g, 46.3 mmol) was added to a slurry of NaH (60% oil dispersion, 2.04 g, 50.9 mmol) in THF (200 ml) and stirred for 15 min, before adding a solution of 4-nitrobenzyl bromide (10.0 g, 46.3 mmol) in THF (100 ml) by cannula. The reaction was stirred for 3 h at room temperature then quenched by the addition of water (100 ml). The aqueous layer was separated and extracted with Et$_2$O (200 ml). The combined organic layers were washed with brine (200 ml), dried (MgSO$_4$) and the solvent evaporated in vacuo to give an off-white solid. Trituration with Et$_2$O/hexane (1:5, 100 ml), removal of the solid by filtration and concentration of the filtrate in vacuo gave an oil which was purified by chromatography (SiO$_2$;EtOAc/hexane 1:3) to give the title compound as an oil (9.4 g), containing about 20% diethyl malonate. δH (CDCl$_3$) 8.15 (2H, d, J 8.8 Hz, Ar—H), 7.39 (2H, d, J 8.7 Hz, Ar—H), 4.25–4.11 (4H, m, CH$_2$CH$_3$), 3.67 (1H, t, J 7.8 Hz, CHCH$_2$Ar), 3.32 (2H, d, J 7.8 Hz, CHCH$_2$Ar) and 1.23 (6H, t, J 7.2 Hz, CH$_2$CH$_3$).

INTERMEDIATE 7

Diethyl-2-(4-aminobenzyl)malonate

Tin (II) chloride (28.8 g, 0.128 mmol) was added to a solution of Intermediate 6 (7.54 g, 25.6 mmol) in EtOH (150 m) and the reaction stirred for 72 h at room temperature. The solvent was removed in vacuo and the residue was treated with 35% aqueous KOH (100 ml), stirred for 30 min and partitioned between EtOAc (200 ml) and water (100 ml). The organic layer was washed with brine, dried (MgSO$_4$) and the solvent evaporated in vacuo to give an oil. Trituration with Et$_2$O/hexane (1:1, 50 ml) gave the title compound (2.86 g, 42%) as an off white solid. δH (CDCl$_3$) 6.99 (2H, d, J 8.4 Hz, Ar—H), 6.60 (2H, d, J 8.4 Hz, Ar—H), 4.15 (4H, m, CH$_2$CH$_3$), 3.57 (1H, t, J 7.8 Hz, CHCH$_2$Ar), 3.57 (2H, br s, NH$_2$), 3.10 (2H, d, J 7.8 Hz, CHCH$_2$Ar) and 1.21 (3H, t, J 7.2 Hz, CH$_2$CH$_3$).

INTERMEDIATE 8

Diethyl-2-{4-[(2,6-dichlorobenzoyl)amino]benzyl}-3-oxopropanoate

A solution of 2,6-dichlorobenzoyl chloride (2.31 g, 11 mmol) in THF (10 ml) was added to a solution of Intermediate 7 (2.86 g, 10.8 mmol) and NMM (1.21 g, 12 mmol) in THF (20 ml). The reaction was stirred for 16 h at room temperature then partitioned between EtOAc (50 ml) and 5% hydrochloric acid (50 ml). The aqueous layer was extracted with EtOAc (50 ml) and the combined organic layers washed with NaHCO$_3$ solution (50 ml) and brine (50 ml), dried (MgSO$_4$) and the solvent removed in vacuo to give an off-white solid that was triturated with isopropyl ether to give the title compound as a white solid, (4.08 g, 86%). δH (CDCl$_3$) 7.54 (2H, d, J 8.5 Hz, Ar—H), 7.38–7.22 (6H, m, Ar—H, NH), 4.234.12 (4H, m, CH$_2$CH$_3$), 3.63 (1H, t, J 7.8 Hz, CHCH$_2$Ar), 3.21 (2H, d, J 7.8 Hz, CHCH$_2$Ar) and 1.23 (6H, t, J 7.1 Hz, CH$_2$CH$_3$).

INTERMEDIATE 9

2-{4-[(2,6-Dichlorobenzoyl)amino]benzyl}-3-ethoxy-3-oxopropanoic Acid

Aqueous KOH (1M, 9.3 ml, 9.3 mmol) was added to a solution of Intermediate 8 (4.05 g, 9.3 mmol) in dioxane (20 ml) and stirred for 3 h. The mixture was acidified to pH1 with 10% hydrochloric acid and extracted with DCM (3×25 ml). The combined organic layers were dried (MgSO)$_4$ and the solvent evaporated in vacuo to give a gum that was purified by chromatography (Si$_2$O DCM/MeOH/AcOH 9:1:0.05) to give the title compound as a foam, (3.71 g, 97%). δH (CDCl$_3$) 7.71 (1H, br s, NH), 7.58 (2H, d, J 8.5 Hz, Ar—H), 7.48–7.20 (5H, m, Ar—H), 4.25–4.14 (2H, m, CH$_2$CH$_3$), 3.66 (1H, t, J 7.7 Hz, CHCH$_2$Ar), 3.24 (2H, d, J 7.7 Hz, CHCH$_2$Ar) and 1.26 (3H, t, J 7.2 Hz, CH$_2$CH$_3$).

INTERMEDIATE 10

Ethyl-3-chloro-2-{4-[(2,6-dichlorobenzoyl)aminogbenzyl-3-oxopropanoate

Thionyl chloride (2.10 g, 17.7 mmol) was added to a solution of Intermediate 9 (1.45 g, 3,5 mmol) in DCM (20 ml) and the reaction stirred at room temperature for 16 h. Volatiles were evaporated in vacuo to give the title compound (1.4 g) as a gummy foam which was used without further purification.

INTERMEDIATE 11

Diethyl 2-{4-[(3,5-Dichloroisonicotinoyl)amino]benzoyl}malonate

A mixture of Intermediate 7 (3.6 g, 13.6 mmol) and triethylamine (2.1 ml, 1.1 equiv) in anhydrous DCM (80 ml)

was cooled to 5°. To this solution was added dropwise a solution of 3,5-dichloropyridyl-4-carbonyl chloride (3.3 g, 1.1 equiv) in 20 ml of DCM. Following addition the solution was stirred at room temperature overnight. The solution was washed with water (3×30 ml), dried (MgSO$_4$) and the solvent evaporated in vacuo to yield the title compound (6 g). δH (CDCl$_3$) 8.5 (2H, s), 7.5 (2H, d, J 8.5 Hz), 7.2 (2H, d, J 8.5 Hz), 4.1 (4H, m), 3.6 (1H, t, J 7.8 Hz), 3.2 (2H, d, J 7.8 Hz) and 1.2 (6H, m).

INTERMEDIATE 12

2-{4-[(3,5-Dichloroisonicotinoyl)amino]benzyl]-3-ethoxy-3-oxopropanoic Acid

A mixture of Intermediate 11 (5 g, 11.4 mmol) and potassium hydroxide (0.63 g, 1 equiv) in 25 ml dioxane/11.5 ml water was stirred for 24 h at room temperature. The mixture was diluted with water (50 ml), washed with DCM (10 ml), acidified with 1N hydrochloric acid solution and the desired product extracted (EtOAc 2×75 ml). The extracts were washed (brine, 30 ml), dried (MgSO$_4$), and the solvent evaporated in vacuo, to yield the title compound (3.2 g) as a white solid. δH (CDCl$_3$) 8.4 (2H, s), 7.4 (2H, d, J 8.5 Hz), 7.2 (2H, d, J 8.5 Hz), 4.0 (2H, q, J 7.8 Hz), 3.5 (1H, t, J 7.8 Hz), 3.0 (2H, d, J 7.8 Hz) and 1.1 (3H, t, J 7.1 Hz).

INTERMEDIATE 13

Ethyl-3-chloro-2-{4-[(3,5-dichloroisonicotinoyl) amino]benzyl}-3-oxopropanoate

Intermediate 12 (1.5 g, 3.8 mmol) was stirred for 24 h in anhydrous DCM (20 ml) and thionyl chloride (1.3 mg, 5 equiv). The solvent and excess thionyl chloride were evaporated in vacuo, azeotroping once with toluene, to yield the title compound (1.6 g) as a gummy solid. δH (CDCl$_3$) 8.9 (2H, s), 7.7 (2H, d, J 8.5 Hz), 7.2 (2H, d, J 8.5 Hz), 4.2 (2H, m), 4.1 (1H, t, J 7.9 Hz), 3.3 (2H, d, J 7.9 Hz) and 1.3 (3H, t, J 7.0 Hz).

EXAMPLE 1

Methyl 2-{4-[(2,6-Dichlorobenzyl)oxy]benzyl}-3-(2,6-dimethoxyanilino)-3-oxopropanoate A solution of 2,6-dimethoxyaniline (0.40 g, 2,6 mmol) in THF (5 ml) was added to a slurry of NaH (60% dispersion in oil, 126 mg, 3.1 mmol) in THF (5 ml), the mixture stirred for 30 mins and a solution of Intermediate 5 (1.05 g, 2,6 mmol) in THF (10 ml) added. The reaction was stirred for 3 h then quenched with water, partitioned between DCM (50 ml) and 10% hydrochloric acid (20 ml). The aqueous layer was extracted with DCM (20 ml) and the combined organic layers washed with NaHCO$_3$ solution (50 ml), dried (MgSO$_4$) and the solvent evaporated in vacuo to give a yellowish foam which was purified by chromatography (SiO$_2$, gradient elution, hexane/EtOAc 3:1 to 1:1) to give the title compound as a white solid, (0.98 g, 73%). δH (CDCl$_3$) 7.37 (1H, br s, NH), 7.35–7.14 (6H, m, Ar—H), 6.94 (2H, m, Ar—H), 6.56 (2H, d, J 8.6 Hz, Ar—H), 5.24 (2H, s, CH$_2$OAr), 3.78 (6H, s, OMe), 3.71 (3H, s, CO$_2$Me), 3.66 (1H, m, C$\underline{H}$CH$_2$) and 3.30 (2H, m, CHC$\underline{H}_2$).

EXAMPLE 2

2-{4-[(2,6-Dichlorobenzyl)oxy]benzyl}-3-(2,6-dimethoxyanilino)-3-oxopropanoic Acid LiOH.H$_2$O (120 mg, 2.9 mmol) was added to a solution of the compound of Example 1 (0.98 g, 1.9 mmol) in THF (10 ml) and water (5 ml) and the reaction stirred at room temperature for 1.5 h, then acidified to pH1 with 10% hydrochloric acid and extracted with DCM (2×25 ml). The combined organic layers were dried (MgSO$_4$) and the solvent evaporated in vacuo to give a white foam that was triturated with DCM/Et$_2$O to give the title compound as a white solid (0.52 g, 54%). δH (DMSO d$_6$) 9.09 (1H, br s, NH), 7.58–7.44 (3H, m, Ar—H), 6.98 (2H, d, J 8.4 Hz, Ar—H), 6.65 (2H, d, J 8.4 Hz, Ar—H), 5.20 (2H, s, CH$_2$OAr), 3.69 (6H, s, OMe), 3.69 (1H, m, C$\underline{H}$CH$_2$) and 3.05 (2H, m, CHC$\underline{H}_2$). m/z (ESI, 60V) 504, 506 (MH$^+$).

EXAMPLE 3

Methyl 2-{4-[(2,6-Dichlorobenzyl)oxy]benzyl}-3-[2-chloro-5-(2-ethoxy-2-oxoethyl)anilino]-3-oxopropanoate A solution of 2-chloro-5-(2-ethoxy-2-oxoethyl)aniline (0.40 g, 1.42 mmol) in THF (5 ml) was added to a solution of Intermediate 5 (1.04 g, 2,6 mmol) and NMM (0.30 g, 3.0 mmol) in THF (10 ml) and stirred for 16 h at room temperature. The reaction was partitioned between EtOAc (25 ml) and 10% hydrochloric acid (20 ml) and the organic layer washed with NaHCO$_3$ solution (2×20 ml), dried (MgSO$_4$) and the solvent evaporated in vacuo to give a yellow gum that was triturated with Et$_2$O to give the title compound as an off white solid (0.45 g, 58%). δH (CDCl$_3$) 8.88 (1H, br s, NH), 8.30 (1H, d, J 1.9 Hz, Ar—H), 7.37–7.21 (6H, m, Ar—H), 7.15 (2H, d, J 8.6 Hz, Ar—H), 6.99 (1H, dd, J 2.1, 8.2 Hz, Ar—H), 6.95 (2H, d, J 8.6 Hz), 5.24 (2H, s, CH$_2$OAr), 4.15 (2H, q, J 7.1 Hz, C$\underline{H}_3$CH$_3$), 3.73 (3H, s, CO$_2$Me), 3.67 (1H, dd, J 6.6, 8.2 Hz, C$\underline{H}_2$CH$_3$)), 3.73 (3H, s, CO$_2$Me), 3.67 (1H, dd, J 6.6, 8.2 Hz, C$\underline{H}$CH$_2$), 3.60 (2H, s, C$\underline{H}_2$CO$_2$Et), 3.30 (2H, m, CHC$\underline{H}_2$) and 1.26 (3H, t, CH$_2$C$\underline{H}_3$).

EXAMPLE 4

3-[5-(Carboxymethyl)-2-chloroanoilino]-2-(4-[(2,6-dichlorobenzyl)oxy]benzyl}-3-oxopropanoic Acid LiOH.H$_2$O (72 mg, 1.72 mmol) was added to a solution of the compound of Example 3 (0.45 g, 0.82 mmol) in THF (10 ml) and water (5 ml). The reaction was stirred for 1 h at room temperature, then acidified to pH1 with 10% hydrochloric acid and extracted with DCM (2×25 ml). The combined organic layers were dried (MgSO$_4$) and solvent evaporated in vacuo to give a gum which was triturated with Et$_2$O/DCM (1:1) to give the title compound as a white solid (180 mg, 41%). δH (DMSO d$_6$) 9.69 (1H, s, NH), 7.57–7.38 (5H, m, ArH), 7.21 (2H, d, J 8.6 Hz, ArH), 7.07 (1H, dd, J 2.1, 8.3 Hz, ArH), 6.97 (2H, d, J 8.6 Hz, Ar—H), 5.18 (2H, s, CH$_2$OAr), 3.93 (1H, m, C$\underline{H}$CH$_2$), 3.56 (2H, s, C$\underline{H}_2$CO$_2$H) and 3.07 (2H, m, CHC$\underline{H}_2$). M/Z (ESI, 60V) 536, 538 (MH$^+$).

EXAMPLE 5

Ethyl-2-{4-[(2,6-dichlorobenzoyl)amino]benzyl}-3-(2,6-dimethoxyanilino)-3-oxopropanoate A solution of Intermediate 10 (0.70 g, 1.68 mmol) in THF (10 ml) was added to a solution of 2,6-dimethoxyaniline (0.20 g, 1.31 mmol) and NMM (0.20 g, 2.0 mmol) in THF (10 ml). The reaction was stirred at room temperature for 16 h then partitioned between water (20 ml) and EtOAc (20 ml), the organic layer separated and washed with 10% hydrochloric acid (10 ml), NaHCO$_3$ solution (10 ml) and brine (10 ml), dried (MgSO$_4$) and the solvent evaporated in vacuo to give a solid which was triturated with boiling EtOAc (10 ml) to give the title compound, (0.59 g, 64%) as a white solid. δH (DMSO $d_6$) 9.10 (1H, s, NH), 7.62–7.47 (5H, m, Ar—H), 7.26 (2H, d, J 8.4, Ar—H), 4.10 (2H, m, CH₂CH₃), 3.82 (1H, t, J 7.4 Hz, CHCH₂), 3.69 (6H, s, OMe), 3.07 (2H, d, J 7.4 Hz, CHCH₂) and 1.19 (3H, t, J 7.1 Hz, CH₂CH₃).

EXAMPLE 6

2-{4-[(2,6-Dichlorobenzoyl)amino]benzyl}-3-(2,6-dimethoxyanilino)-3-oxopropanoic Acid A solution of the compound of Example 5 (0.59 g, 1.1 mmol) in EtOH (5 ml), THF (2 ml) and water (2 ml) was treated with KOH (1M aqueous solution, 1.62 ml, 1.62 mmol) and the reaction stirred for 2.5 h. The mixture was concentrated in vacuo and acidified to pH1 with 10% hydrochloric acid, to give a white precipitate which was isolated by filtration and washed with water, triturated with boiling MeOH and washed with Et₂O to give the title compound as a white solid (300 mg, 54%). δH (DMSO $d_6$) 10.65 (1H, s, NH), 9.04 (1H, s, NH), 7.6–7.46 (5H, m, Ar—H), 7.28–7.16 (3H, m, Ar—H), 6.65 (2H, d, J 8.4 Hz, Ar—H), 3.74 (1H, m, CHCH₂), 3.68 (6H, s, OMe), 3.30 (1H, m, CHCH$_A$H$_B$) and 3.06 (1H, m, CHCH$_A$H$_B$). m/z (ESI, 60V) 517, 519 (MH⁺).

EXAMPLE 7

Ethyl 3-(2,6-Dichloroanilino)-2-{3-[(3,5-dichloroisonicotinoyl)amino]benzyl}-3-oxopropanoate Intermediate 13 (350 mg, 0.8 mmol) in anhydrous DCM (2 ml) was added dropwise to a mixture of 2,6-dichloroaniline (133 mg, 1 equiv) and triethylamine (0.12 ml, 1.1 equiv), dissolved in DCM (10 ml) at 5°. The mixture was stirred for 16 h at room temperature, then quenched with water (2 ml) The solvent was removed, and the residue dissolved in EtOAc. The resulting solution was washed with water, (2×10 ml), brine (10 ml), dried (MgSO₄) and the solvent evaporated in vacuo. The residue was slurried in Et₂O and the title compound (360 mg) isolated by filtration. δH (CDCl₃) 8.5 (2H, s), 7.5 (2H, d, J 8.5 Hz), 7.25 (2H, d, J 8.5 Hz), 7.2 (2H, d, J 8.5 Hz), 7.1 (1H, t, J 8.5 Hz), 4.1 (2H, q, J 7.0 Hz), 3.7 (1H, t, J 7.9 Hz), 3.2 (2H, d, J 7.9 Hz) and 1.1 (3H, t, J 7.0 Hz). m/z/ (ESI, 60V) 554 (M+H)⁺.

EXAMPLE 8

Ethyl-3-(2,6-dimethoxyanilino)-2-{4-[(3,5-dichloroisonicotinoyl)amino]benzyl}-3-oxopropanoate The title compound was prepared using the method of Example 6, substituting 2,6-dimethoxyaniline for 2,6-dichloroaniline. The title compound was isolated as white solid, (64%). δH (CDCl₃+few drops CD₃OD) 8.5 (2H, s), 7.5 (2H, broad signal), 7.2 (2H, broad signal), 7.1 (1 H, broad triplet), 6.5 (2H, d, J 8.4 Hz), 4.1 (2H, broad signal), 3.7 (6H, s), 3.6 (1H, broad signal), 3.3 (2H, broad signal), 3.0 (3H, s) and 1.2 (3H, t, J 7.2 Hz). m/z (ESI, 60V) 546 (M+H)⁺.

EXAMPLE 9

Ethyl 2-{4-[(3,5-Dichloroisonicotinoyl)amino]benzyl}-3-(3,5-dichloro-4-pyridinyl)-3-oxopropanoate 3,5 Dichloro-4-aminopyridine (190 mg, 1.2 mmol) dissolved in anhydrous THF (5 ml) was added dropwise to a suspension of sodium hydride (68%, 150 mg, 3.2 equiv) in anhydrous THF (2 ml) at 5°. Following addition the mixture was stirred at room temperature for 10 min, recooled to 5° and Intermediate 13 (0.5 g, 1 equiv) in anhydrous THF (5 ml) was added in one portion. The mixture was stirred at room temperature for 16 h, quenched with water, and diluted with EtOAc (50 ml). The organic layer was isolated and washed with water (2×10 ml), brine (10 ml) dried (MgSO₄), and the solvent removed in vacuo. The residue was slurried in Et₂O and the title compound (300 mg) was isolated by filtration. δH (CD₃OD+few drops DMSO $d_6$) 8.7 (2H, s), 8.6 (2H, s), 7.6 (2H, d, J 8.9 Hz), 7.4 (2H, d, J 8.9 Hz), 4.3 (2H, d, J 8.9 Hz), 7.4 (2H, d, J 8.9 Hz), 4.3 (2H, q, J 7.2 Hz), 4.1 (1H, m), 3.3 (2H, m) and 1.3 (34H, t, J 7.2 Hz). m/z (ESI, 60V) 554 (M+H)⁺.

EXAMPLE 10

3-(2,6-Dichloroanilino)-2-{4-[3,5-dichloroisonicotinoyl)amino]benzyl}-3-oxopropanoic Acid The compound of Example 7 (350 mg, 0.6 mmol) and LiOH.H₂O (40 mg, 1.5 equiv) were stirred for 16 h in a mixture of MeOH (10 ml), water (5 ml) and THF (5 ml). The solvents were removed in vacuo and the residue dissolved in water (5 ml). The solution was acidified and extracted with EtOAc (3×20 ml). The combined extracts were washed with water (2×10 ml), dried (MgSO₄) and the solvent removed in vacuo to yield the title compound (290 mg) as a white solid. δH (DMSO) 10.8 (1H, s), 10.1 (1H, s), 8.8 (2H, s), 7.6 (2H, d, J 8.5 Hz), 7.5 (2H, d, J 8.0 Hz), 7.3 (3H, m), 3.8 (1H, t) and 3.1 (2H, m). m/z (ESI, 60V) 526 (MH)⁺.

The compounds of Examples 11 and 12 were prepared in a similar manner to the compound of Example 10:

EXAMPLE 11

3-(2,6-Dimethoxyanilino)-2-{4-[(3,5-dichloroisonicotinoyl)amino]benzyl}-3-oxopropanoic Acid From the compound of Example 8. The title compound was isolated as a white solid (69%). δH (DMSO $d_6$) 10.8 (1H, s), 8.7 (2H, s), 7.5 (2H, d, J 8.4 Hz), 7.3 (2H, d, J 8.4 Hz), 7.2 (1 H, t, J 8.4 Hz), 6.6 (2H, d, J 8.4 Hz), 3.7 (7H, s) and 3.0 (2H, d, J 7.5 Hz). m/z (ESI) 518 (M+H)⁺.

EXAMPLE 12

2-{4-[(3,5-Dichloroisonicotinoyl)amino]benzyl}-3-[(3,5-dichloro-4-pyridinyl)amino]-3-oxopropanoic Acid From the compound of Example 9. The title compound was isolated as a white solid (20%). δH (DMSO $d_6$) 10.8 (1H, s), 10.4 (1H, s), 8.8 (2H, s), 8.6 (2H, s), 7.6 (2H, d, J 8.5 Hz), 7.3 (2H, d, J 8.5 Hz), 3.9 (1H, t) and 3.2 (2H, m). m/z (ESI) 526 (M+H)⁺.

The following assays can be used to demonstrate the potency and selectivity of the compounds according to the invention. In each of these assays an IC₅₀ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-dependent Jurkat Cell Adhesion to VCAM-Ig 96 well NUNC plates were coated with F(ab)₂ fragment goat anti-human IgG Fcγ-specific antibody [Jackson Immuno Research 109-006-098: 100 μl at 2 μg/ml in 0.1M NaHCO₃, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 μl containing 2.5×10⁵ Jurkat cells in the presence or absence of titrated test compounds.

Each plate was washed (2×) with medium and the adherent cells were fixed with 100 μl methanol for 10 minutes followed by another wash. 100 μl 0.25% Rose Bengal (Sigma R4507) in PBS was added for 5 minutes at room temperature and the plates washed (3×) in PBS. 100 μl 50% (v/v) ethanol in PBS was added and the plates left for 60 min after which the absorbance (570 nm) was measured.

$\alpha_4\beta_7$ Integrin-dependent JY Cell Adhesion to MAdCAM-Ig

This assay was performed in the same manner as the $\alpha_4\beta_1$ assay except that MAdCAM-Ig (150 ng/ml) was used in place of 2d VCAM-Ig and a sub-line of the β-lympho blastoid cell-line JY was used in place of Jurkat cells. The IC₅₀ value for each test compound was determined as described in the $\alpha_4\beta_1$ integrin assay.

$\alpha_5\beta_1$ Integrin-dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C. in a total volume of 200 μl containing 2.5×10⁵ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-Dependent Human Polymorphonuclear Neutrophils Adhesion to Plastic 96 well tissue culture plates were coated with RPMI 1640/10% FCS for 2 h at 37° C. 2×10⁵ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H₂O₂ (Sigma) and 50 μg/ml TMB (Boehringer Mannheim) in 0.1M sodium acetate/citrate buffer, pH 6.0 and absorbance measured at 630 nm.

$\alpha IIb/\beta_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10⁸/ml in autologous plasma. Cuvettes contained equal volumes of PRP and filtered Tyrode's buffer (g/liter: NaCl 8.0; MgCl₂.H₂O 0.427; CaCl₂ 0.2; KCl 0.2; D-glucose 1.0; NaHCO₃ 1.0; NaHPO₄.2H₂O 0.065). Aggregation was monitored following addition of 2.5 μM ADP (Sigma) in the presence or absence of inhibitors.

In the above assays the preferred compounds of the invention generally have IC₅₀ values in the $\alpha_4\beta_1$ and $\alpha_4\beta_7$ assays of 1 μM and below. In the other assays featuring a integrins of other subgroups the same compounds had IC₅₀ values of 50 μM and above thus demonstrating the potency and selectivity of their action against $\alpha_4$ integrins.

What is claimed is:

1. A compound of formula (1):

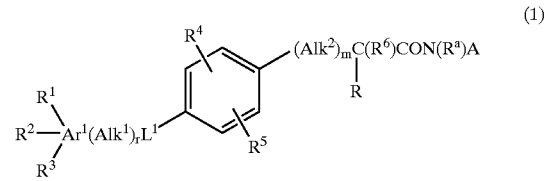

wherein

Ar¹ is an aromatic or heteroaromatic group;

R¹, R², R³, R⁴ and R⁵ which may be the same or different is each an atom or group —L²(Alk³)ₜL³(R⁷)ᵤ in which L² and L³ which may be the same or different is each a covalent bond or a linker atom or group, t is zero or the integer 1, u is an integer 1, 2 or 3, Alk³ is an aliphatic or heteroaliphatic chain and R⁷ is a hydrogen or halogen atom or a group selected from alkyl, —OR⁸ (where R⁸ is a hydrogen atom or an optionally substituted alkyl group), —SR⁸, —NR⁸R⁹ (where R⁹ is as just defined for R⁸ and may be the same or different), —NO₂, —CN, —CO₂R⁸, —SO₃H, —S(O)R⁸, —SO₂R⁸, —OCO₂R⁸, —CONR⁸R⁹, —OCONR⁸R⁹, —CSNR⁸R⁹, —COR⁸, —OCOR⁸, —N(R⁸)COR⁹, —N(R⁸)CSR⁹, —SO₂N(R⁸)(R⁹), —N(R⁸)SO₂R⁹, —N(R⁸)CON(R⁹)(R¹⁰), (where R¹⁰ is a hydrogen atom or an optionally substituted alkyl group) —N(R⁸)CSN(R⁹)(R¹⁰) or —N(R⁸)SO₂N(R⁹)(R¹⁰);

Alk¹ is an optionally substituted aliphatic or heteroaliphatic chain;

L¹ is a covalent bond or a linker atom or group;

Alk² is a straight or branched alkylene chain;

m is zero or an integer 1;

R⁶ is a hydrogen atom or a methyl group;

r is zero or the integer 1;

R is a carboxylic acid (—CO₂H) or a carboxylic acid ester or amide;

Rᵃ is a hydrogen atom or a methyl group;

A is an optionally substituted aliphatic, heteroaliphatic, cycloaliphatic, polycycloaliphatic, heterocycloaliphatic, polyheterocycloaliphatic, aromatic or heteroaromatic group;

and the salts solvates, hydrates and N-oxides thereof.

2. A compound according to claim 1 in which R is a —CO₂H group.

3. A compound according to claim 1 in which Alk² is a —CH₂— chain and m is the integer 1.

4. A compound according to claim 1 in which R⁶ and Rᵃ is each a hydrogen atom.

5. A compound according to claim 1 in which Ar¹ is a phenyl, pyridyl or pyrimidinyl group, wherein R¹ and R² is each a halogen atom or alkyloxy or haloalkyloxy group and R³ is hydrogen.

6. A compound according to claim 1 in which (Alk¹)ᵣL¹ is a —CH₂O— or —CON(R¹¹)— group.

7. A compound according to claim 1 in which A is an optionally substituted phenyl or pyridyl group.

8. A compound which is:

3-(2,6-Dichloroanilino)-2-{4-[(3,5-dichloroisonicotinoyl)amino]benzyl}-3-oxopropanoic acid;

3-(2,6-Dimethoxyanilino)-2-{4-[(3,5-dichloroisonicotinoyl)amino]benzyl}-3-oxopropanoic acid;

2-{4-[(3,5-Dichloroisonicotinoyl)amino]benzyl}-3-[(3,5-dichloro-4pyridinyl)amino]-3-oxopropanoic acid;

2-{4-[(2,6-Dichlorobenzoyl)amino]benzyl}-3-(2,6-dimethoxyanilino)-3-oxopropanoic acid;

2-{4-[(2,6-Dichlorobenzyl)oxy]benzyl}-3-(2,6-dimethoxyanilino)-3-oxopropanoic acid;

and the salts solvates, hydrates and N-oxides thereof.

9. A pharmaceutical composition comprising a compound according to claim 1 together with one or more pharmaceutically acceptable carriers, excipients or diluents.

* * * * *